US00PP21076P3

(12) United States Plant Patent
Lyons

(10) Patent No.: US PP21,076 P3
(45) Date of Patent: Jun. 22, 2010

(54) RED MAPLE TREE NAMED 'KATIE COLE'

(50) Latin Name: *Acer rubrum*
Varietal Denomination: Katie Cole

(76) Inventor: Robert S. Lyons, 2101 Old Mill Rd., Madison, OH (US) 44057

( * ) Notice: Subject to any disclaimer, the term of this patent is extended or adjusted under 35 U.S.C. 154(b) by 0 days.

(21) Appl. No.: 12/284,183

(22) Filed: Sep. 19, 2008

(65) Prior Publication Data

US 2010/0077521 P1 Mar. 25, 2010

(51) Int. Cl.
*A01H 5/00* (2006.01)

(52) U.S. Cl. ..... Plt./224

(58) Field of Classification Search ..... Plt./224
See application file for complete search history.

*Primary Examiner*—Annette H Para
(74) *Attorney, Agent, or Firm*—Renner, Otto, Boisselle & Sklar, LLP

(57) ABSTRACT

A red maple tree named 'Katie Cole', a medium tree distinguished by the prolonged red coloration of its new leaf growth.

2 Drawing Sheets

Latin name of the genus and species including the variety denomination of the plant claimed: The plant claimed relates to a new and distinct variety of red maple, botanically known as *Acer rubrum,* and known by the cultivar name Katie Cole.

This new cultivar was found mixed with a quantity of trees of *Acer rubrum* 'Franksred' grown at Sunleaf Nursery in Madison, Ohio. This new cultivar was noted as distinctive because of the striking red leaves on the expanding shoots that caused it to stand out from the others.

The Katie Cole variety is the only variant of red maple I am aware of that displays the prolonged red coloration of its new leaf growth. Leaves of red maple are often red as they emerge from the bud, but this color rapidly changes to the normal green as the leaves expand. The leaves of the Katie Cole variety maintain a saturated red color from when they emerge until they are fully expanded. This character provides an additional period of high ornamental interest for this variety, in addition to the red fall leaf coloration period that is normally a feature of this species.

The original Katie Cole cultivar, which is 8 years old, is approximately 14 feet tall, and has a single main trunk and pyramidal crown of ascending branches.

The Katie Cole cultivar has been asexually reproduced at Sunleaf Nursery in Madison, Ohio, by means of grafting and budding, and plants propagated by this method have displayed the same unique characteristics of the original plant.

Figure 1:
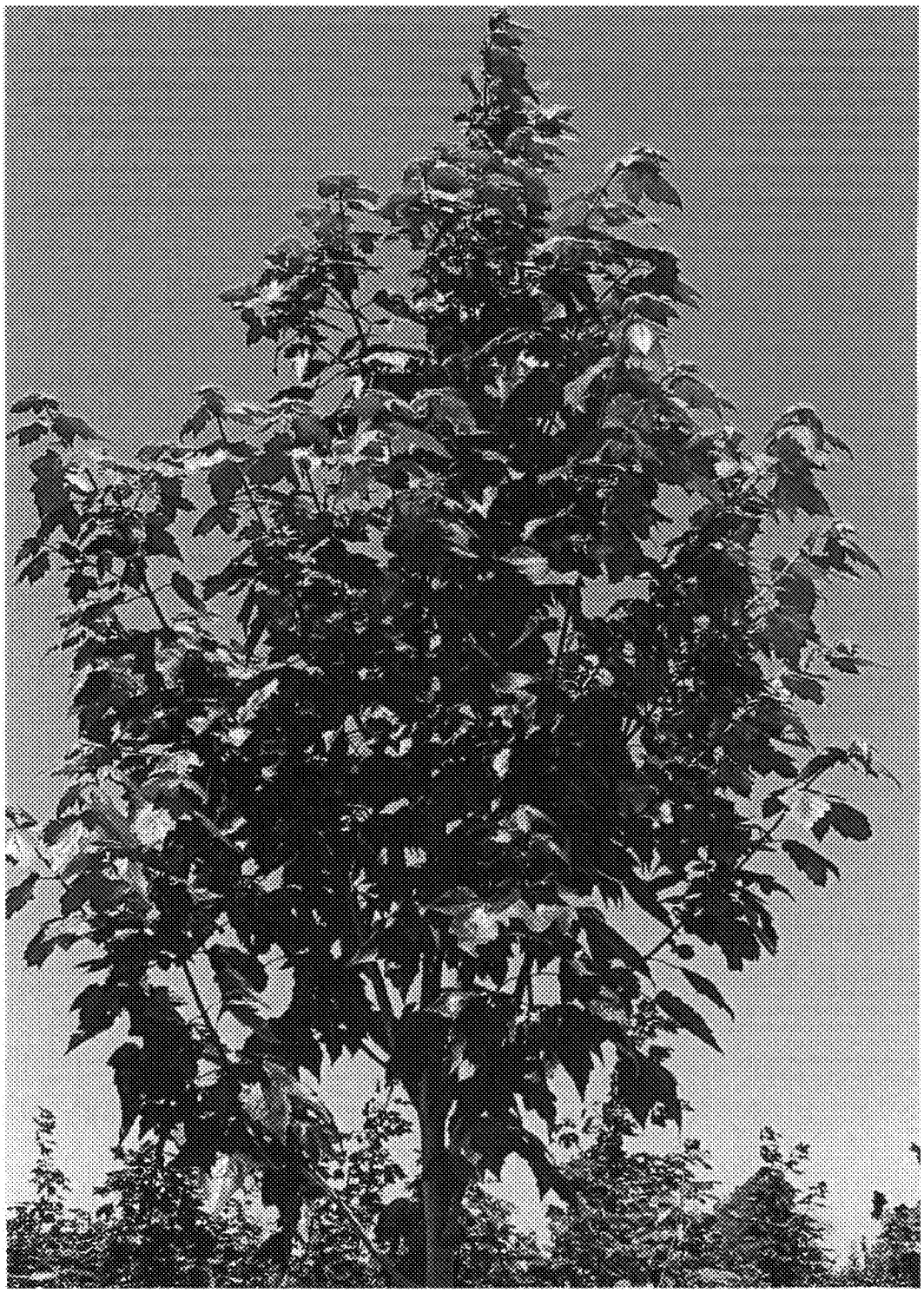
FIG. 1 is a colored photograph illustrating the overall appearance of the cultivar Katie Cole in the summer.
Figure 2:
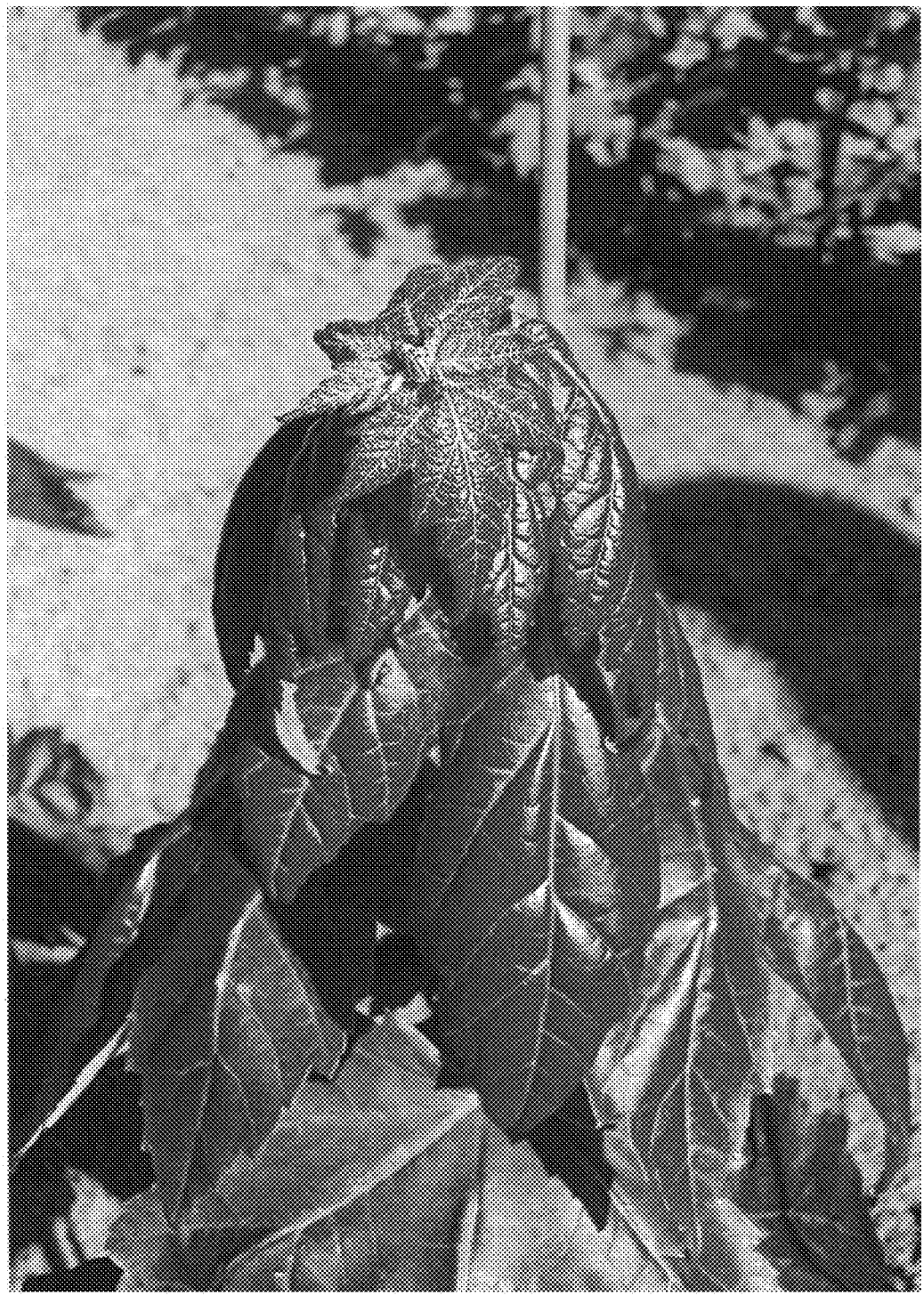
FIG. 2 is a colored photograph illustrating the prolonged red coloration of the new leaf growth of Katie Cole in the summer.

All of the drawing figures show the colors as truly as is reasonably possible to obtain in colored reproductions of this type.

The following is a detailed description of my new cultivar, Katie Cole. In all cases, where color is different from the typical and is considered a distinguishing feature of this variety, reference is made to specific colors on The R.H.S. Colour Chart (1986 ed.) published by The Royal Horticultural Society, London, England. Here follows a detailed description of the characteristics of this cultivar, as displayed by specimens grown at Madison, Lake County, Ohio. Coloration of leaves and bark may be variable, due to conditions of nutrition, stress, age of plant, location on plant and the presence/absence of sun/shade. Plant part comparisons have been made using samples taken from a mature plant where growth rates and characteristics are considered typical.

BOTANICAL DESCRIPTION

Parentage: Unknown — discovered in a group of nursery trees of *Acer rubrum* 'Franksred'.

Hardiness: Hardy in USDA Hardiness Zone 4b (−25° F. minimum).

Growth rate: Moderate. The original specimen at 8 years old in Madison, Ohio was approximately 14 feet tall. The increase in length of the stems of the original specimen over the past growing season at 9 years old in Madison, Ohio averaged 21 inches (53 cm). Young nursery trees under irrigation produced annual shoot growth at 24 to 30 inches (61 to 76 cm.).

Habit: Deciduous tree with single main trunk and pyramidal crown of ascending branches. The angles of the primary ranches range from 45° to 60° from the vertical main stem.

Bark: The bark on the main stem and branches in their third year or older is smooth and light gray (Black Group 202 D).

Leaves: Oppositely arranged, deciduous, simple palmately 3-lobed. The margins of the leaves are doubly serrate. Leaf blade 7.15–13 cm. in length, 5–11 cm. across, petioles 2.5–5 cm. in length. Color of expanding leaves Red-Purple Group 59A becoming Greyed-Purple Group 183A at near full expansion. Color of the upper (adaxial) surface of mature leaves Green Group 137A, lower (abaxial) surface Greyed-Green Group 191C. At full leaf expansion, the petiole is colored Red Group 46A along its entire length and on all sides. This color extends into and persists in the primary veins on the upper (adaxial) surface of the leaves and primary and secondary veins on the undersde (abaxial surface) of the leaves. In fall, color of the upper leaf surface becomes Greyed-Purple Group 187A at peak coloration.

Twigs: Mature first year twigs are slender, smooth, reddish (Greyed-Purple Group 182A) and bear numerous (152 per 2 inch (5 cm.) length of stem) lenticels. The lenticels are white (White Group 155D) to buff (Greyed-Orange Group 167D) in color, irregulary orbicular or oval to elliptical in shape, and 0.5 to 2.5 mm in length. Mature second year stems are gray (between Black Group 202C and 202D) and the lenticels, being more or less the same color, are obscured.

Flowers: Flowers are borne in axillary umbels. Flowers are stalked, each flower with 5 petals and 5–8 exserted stamens. The open flowers are bright red (Red Group 45B. To date, female flowers have not been produced.

Seeds: Seeds are not produced. This is to be expected, as the only flowers so far produced have been male.

I claim:

1. A red maple tree named 'Katie Cole', as described and illustrated, a medium tree distinguished by the prolonged red coloration of its new leaf growth.

* * * * *